United States Patent [19]

Maurer et al.

[11] 4,155,999
[45] May 22, 1979

[54] PESTICIDALLY ACTIVE O-ALKYL-O-[6-TERT.-BUTYL-PYRIMIDIN(-4)YL]-(THIONO)(THIOL)-PHOSPHORIC(-PHOSPHONIC) ACID ESTERS

[75] Inventors: Fritz Maurer; Hans-Jochem Riebel; Rolf Schröder, all of Wuppertal; Wolfgang Behrenz, Overath; Ingeborg Hammann, Cologne; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 829,552

[22] Filed: Aug. 31, 1977

[30] Foreign Application Priority Data

Sep. 2, 1976 [DE] Fed. Rep. of Germany ....... 2639433

[51] Int. Cl.² ............................ A01N 9/36; C07F 9/65
[52] U.S. Cl. .................................. 424/246; 544/243; 544/319
[58] Field of Search .................... 260/251 P; 424/200; 544/243

[56] References Cited
U.S. PATENT DOCUMENTS 2,754,243  7/1956  Gysin et al. ........................ 424/200
3,159,630  12/1964  Rigterink ........................ 260/256.4 E
3,216,894  11/1965  Lorenz et al. ........................ 424/200
3,886,156  5/1975  Hofer et al. ........................ 260/251 P
3,951,975  4/1976  Hofer et al. ........................ 260/251 P Primary Examiner—Donald G. Daus
Assistant Examiner—Diana G. Rivers
Attorney, Agent, or Firm—Sprung, Felfe, Horn, Lynch & Kramer

[57] ABSTRACT

O-Alkyl-O-[6-tert.-butyl-pyrimidin(4)yl](thiono)(thiol)-phosphoric(phosphonic) acid esters of the formula

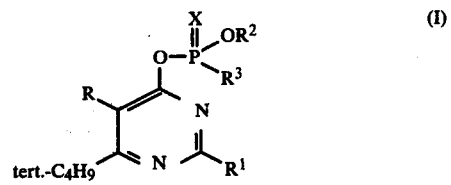

in which
R is hydrogen, halogen or alkyl,
$R^1$ is hydrogen or alkyl,
$R^2$ is alkyl,
$R^3$ is alkyl, alkoxy, alkylthio or phenyl, and
X is oxygen or sulphur. which possess insecticidal and acaricidal properties.

10 Claims, No Drawings

PESTICIDALLY ACTIVE O-ALKYL-O-[6-TERT.-BUTYL-PYRIMIDIN(4)YL]-(THIONO)(THIOL)-PHOSPHORIC(PHOSPHONIC) ACID ESTERS

The present invention relates to and has for its objects the provision of particular new O-alkyl-O-[6-tert.-butyl-pyrimidin(4)yl]-(thiono)(thiol)-phosphoric(phosphonic) acid esters which possess insecticidal and acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from U.S. Pat. Nos. 3,216,894 and 3,886,156 that certain methyl-substituted pyrimidinylthionophosphoric(phosphonic) acid esters, for example O-methyl- and O-ethyl-O-[2,6-dimethyl-pyrimidin(4)-yl]-ethane- and -methane-thionophosphonic acid esters and O,O-diethyl-O-[2,5-dimethylthio-6-methyl-pyrimidin(4)yl]-thionophosphoric acid ester, possess insecticidal and acaricidal properties.

The present invention now provides, as new compounds, the pyrimidinyl(thiono)(thiol)-phosphoric(phosphonic) acid esters of the general formula

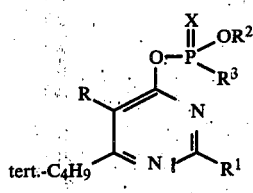

(I)

in which
R is hydrogen, halogen or alkyl,
R¹ is hydrogen or alkyl,
R² is alkyl,
R³ is alkyl, alkoxy, alkylthio or phenyl, and
X is oxygen or sulphur.

Preferably, R represents hydrogen or chlorine, R¹ represents hydrogen or straight-chain or branched alkyl with 1 to 6 (especially 1 to 4) carbon atoms, R² represents straight-chain or branched alkyl with 1 to 6 (especially 1 to 4) carbon atoms, R³ represents straight-chain or branched alkoxy or alkylthio each with 1 to 6 (especially with 1 to 4) carbon atoms or straight-chain or branched alkyl with 1 to 8 (especially 1 to 5) carbon atoms, or phenyl and X represents sulphur. In a preferred sub-group R² is ethyl while R³ is S-n-propyl.

Surprisingly, the pyrimidinyl(thiono)(thiol)-phosphoric(phosphonic) acid esters according to the invention exhibit a better insecticidal and acaricidal action than the known methyl-substituted pyrimidinylthionophosphoric(phosphonic) acid esters of analogous structure and of the same type of action. The compounds according to the present invention thus represent a genuine enrichment of the art.

The invention also provides a process for the preparation of a pyrimidinyl(thiono)(thiol)-phosphoric (phosphonic) acid ester of the formula (I) in which a (thiono)(thiol)-phosphoric(phosphonic) acid ester halide of the general formula

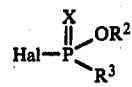

(II), in which
R², R³ and X have the above-mentioned meanings and
Hal represents halogen, preferably chlorine, is reacted, if appropriate in the presence of a solvent or diluent, with a 4-hydroxy-6-tert.-butyl-pyrimidine of the formula

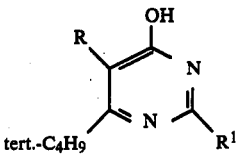

(III), in which
R and R¹ have the above-mentioned meaning, the latter being employed as such in the presence of an acid acceptor or in the form of an alkali metal salt, alkaline earth metal salt or ammonium salt.

If, for example, O-sec.-butyl-ethane-thiono-phosphonic acid ester chloride and 2-n-propyl-4-hydroxy-5-methyl-6-tert.-butyl-pyrimidine are used as starting materials, the course of the reaction can be represented by the following equation:

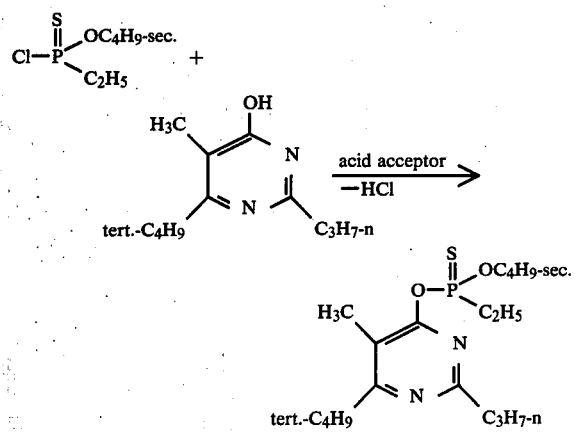

The (thiono)(thiol)-phosphoric(phosphonic) acid ester halides (II) to be used as starting materials are known and can readily be prepared, even on an industrial scale, in accordance with processes known from the literature. The following may be mentioned as individual examples thereof: O,O-dimethyl-, O,O-diethyl-, O,O-di-n-propyl-, O,O-di-isopropyl-, O,O-di-n-butyl-, O,O-di-iso-butyl-, O,O-di-sec.-butyl-, O-methyl-O-ethyl-, O-methyl-O-n-propyl-, O-methyl-O-iso-propyl-, O-methyl-O-n-butyl, O-methyl-O-isobutyl-, O-methyl-O-sec.-butyl-, O-ethyl-O-n-propyl-, O-ethyl-O-iso-propyl-, O-ethyl-O-n-butyl-, O-ethyl-O-sec.butyl-, O-ethyl-O-iso-butyl-, O-n-propyl-O-butyl- and O-iso-propyl-O-butyl-thionophosphoric acid diester chloride, as well as O,S-dimethyl-, O,S-diethyl-, O,S-di-n-propyl-, O,S-di-isopropyl-, O,S-di-n-butyl-, O,S-di-iso-butyl-, O-ethyl-S-n-propyl-, O-ethyl-S-iso-propyl-, O-ethyl-S-n-butyl-, O-ethyl-S-sec.-butyl-, O-n-propyl-S-ethyl-, O-n-propyl-S-iso-propyl, O-n-butyl-S-n-propyl- and O-sec.-butyl-S-ethylthionothiolphosphoric acid diester chloride and O-methyl-, O-ethyl-, O-n-propyl-, O-iso-propyl-, O-n-butyl-, O-iso-butyl- and O-sec.-butyl-methane-, ethane-, n-propane-, iso-propane-, n-butane-, iso-butane-, tert.-butane-, sec.-butane-, n-pentane- and benzene-thionophosphonic acid ester chloride.

The 4-hydroxy-6-tert.-butyl-pyrimidines (III), also to be used as starting materials, can also be prepared in accordance with processes known from the literature, for example by condensing acylamidine hydrochlorides with pivaloylacetic acid alkyl ester derivatives, if appropriate in the presence of an alcoholate. The following may be mentioned as individual examples thereof: 6-tert.-butyl- and 5-chloro-6-tert.-butyl-4-hydroxy-pyrimidine, as well as 2-methyl-, 2-ethyl-, 2-n-propyl-, 2-iso-propyl-, 2-n-butyl-, 2-sec.-butyl-, 2-iso-butyl-, 2-tert.-butyl-, 2-methyl-5-chloro-, 2-ethyl-5-chloro-, 2-n-propyl-5-chloro-, 2-iso-propyl-5-chloro-, 2-n-butyl-5-chloro-, 2-iso-butyl-5-chloro- and 2-sec.-butyl-5-chloro-4-hydroxy-6-tert.-butyl-pyrimidine.

The process for the preparation of the compounds according to the invention is preferably carried out in the presence of a suitable solvent or diluent. Virtually all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane, ketones, for example acetone, methyl ethyl ketone, methyl isopropyl ketone and methyl isobutyl ketone; and nitriles; such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate, ethylate and tert.-butylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at from 0° to 120° C. preferably at from 20° to 60° C.

In general, the reaction is allowed to take place under normal pressure.

To carry out the process, the starting materials are preferably employed in equimolar amounts. An excess of one or other reactant produces no significant advantages.

In general, the reactants are combined in one of the stated solvents and are stirred for one or more hours, in most cases at an elevated temperature, to complete the reaction. After cooling, an organic solvent, for example toluene, is added to the mixture and the organic phase is worked up in the usual manner by washing, drying, and distilling off the solvent.

The new compounds are frequently obtained in the form of oils, which in most cases cannot be distilled without decomposition, but are freed from the last volatile constituents by so-called "slight distillation", that is to say by prolonged heating under reduced pressure to moderately elevated temperatures, and are purified in this way. They are characterized by the refractive index.

As already mentioned, the compounds according to the present invention are distinguished by an excellent insecticidal and acaricidal activity. They are therefore active against plant pests, pests harmful to health and pests of stored products and combine a low phytotoxicity with a good action against sucking and biting insects and against mites.

For this reason, the compounds according to the invention can be employed successfully as pesticides in plant protection and in the hygiene field and the field of protection of stored products.

The compounds according to the present invention can also be used in the field of veterinary medicine, since they are also active against animal parasites, in particular ectoparasites such as parasitic fly larvae.

The active compounds are well tolerated by plants, have a favorable level of toxicity to warm-blooded animals, and can be used for combating arthropod pests, especially insects and acarids, and nematode pests which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Pyllocnistis citrella,* Agrotis spp., Euxoa spp., Feltia spp., *Earias insulana*, Heliothis spp., *Laphygma exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., Meligethes aeneus, Ptinus spp., *Niptus hololeucus, Gibbium psylloides*, Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro*, Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoriptes spp., Chlorioptes spp., Sarcoptes spp., Tarsonemus spp., *Bryobia praetiosa,* Panonychus spp. and Tetranychus spp..

The plant-parasitic nematodes include Pratylenchus spp., Radopholus similis, Ditylenchus dipsaci, Tylenchulus semipenetrans, Heterodera spp., Meloidogyne spp., Aphelenchoides spp., Longidorus spp., Xiphinema spp., and Trichodorus spp..

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. dichlorodifluoromethane and trichlorofluoromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane), etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides, or nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

EXAMPLE 1

The 4-hydroxy-6-tert.-butyl-pyrimidines (III) required as starting materials could be prepared, for example, as described below:

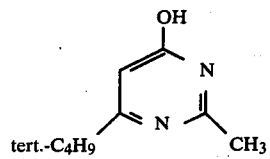

A suspension of 21.6 g (0.4 mol) of sodium methylate, 19.4 g (0.2 mol) of acetamidine hydrochloride, 34.4 g (0.2 mol) of pivaloylacetic acid ethyl ester and 100 ml of methanol was heated for 10 hours under reflux and then evaporated, and the residue was taken up in 350 ml of water. Concentrated hydrochloric acid was added to the aqueous solution, while cooling with ice, to a pH of about 6, and the mixture was then extracted twice with 200 ml of methylene chloride each time. The combined methylene chloride extracts were dried over sodium sulphate and then concentrated. 21 g (63% of theory) of 2-methyl-4-hydroxy-6-tert.-butyl-pyrimidine were obtained in the form of colorless crystals of melting point 131°–132° C.

The following compounds of the formula

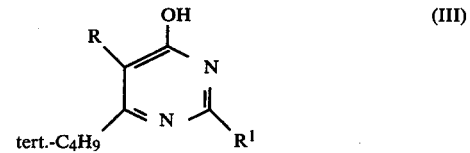

could be prepared analogously:

TABLE 1

| R | R$^1$ | Yield (% of theory) | Melting point, °C. |
|---|---|---|---|
| H | C$_2$H$_5$ | 79 | 46 |
| H | H | 45 | 218 |
| H | C$_3$H$_7$-iso | 62 | 113 |

EXAMPLE 2

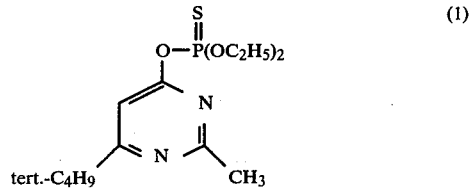

18.8 g (0.1 mol) of O,O-diethylthionophosphoric acid diester chloride were added dropwise to a mixture of 16.6 g (0.1 mol) of 2-methyl-4-hydroxy-6-tert.-butyl-pyrimidine, 14.5 g (0.105 mol) of potassium carbonate and 200 ml of acetonitrile. The batch was warmed to 40° C. for 3 hours and was then cooled, and the reaction mixture was poured into 300 ml of toluene. The toluene solution was washed with saturated sodium bicarbonate solution and water, dried over sodium sulphate and concentrated. After slight distillation, 22 g (69% of theory) of O,O-diethyl-O-[2-methyl-6-tert.-butyl-pyrimidin(4)yl]-thionophosphoric acid ester were obtained in the form of a yellow oil having a refractive index $n_D^{23}$ of 1.4930.

The following compounds of the formula

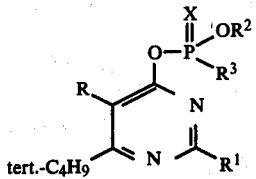

could be synthesized analogously:

TABLE 2

| Compound No. | R | $R^1$ | $R^2$ | $R^3$ | X | Yield (% of theory) | Refractive index: |
|---|---|---|---|---|---|---|---|
| 2 | H | $CH_3$ | $C_2H_5$ | $C_2H_5$ | S | 70 | $n_D^{23}$:1.5060 |
| 3 | H | $CH_3$ | $C_2H_5$ | $CH_3$ | S | 74 | $n_D^{23}$:1.5090 |
| 4 | H | $CH_3$ | $C_3H_7$-iso | $CH_3$ | S | 70 | $n_D^{23}$:1.5035 |
| 5 | H | $CH_3$ | $C_3H_7$-n | $OCH_3$ | S | 54 | $n_D^{23}$:1.4968 |
| 6 | H | $CH_3$ | $CH_3$ | $OCH_3$ | S | 40 | $n_D^{23}$:1.5048 |
| 7 | H | $CH_3$ | $C_2H_5$ | $OC_2H_5$ | O | 51 | $n_D^{23}$:1.4679 |
| 8 | H | $CH_3$ | $C_2H_5$ | phenyl | S | 81 | $n_D^{22}$:1.5540 |
| 9 | H | $C_2H_5$ | $C_2H_5$ | $OC_2H_5$ | S | 64 | $n_D^{23}$:1.4873 |
| 10 | H | $C_2H_5$ | $C_2H_5$ | $C_2H_5$ | S | 76 | $n_D^{23}$:1.4977 |
| 11 | H | $C_2H_5$ | $CH_3$ | $OCH_3$ | S | 39 | $n_D^{23}$:1.4909 |
| 12 | H | $C_2H_5$ | $C_3H_7$-iso | $CH_3$ | S | 76 | $n_D^{23}$:1.4948 |
| 13 | H | $C_2H_5$ | $C_2H_5$ | $SC_3H_7$-n | S | 66 | $n_D^{23}$:1.5186 |
| 14 | H | $C_2H_5$ | $C_2H_5$ | phenyl | S | 73 | $n_D^{23}$:1.5404 |
| 15 | H | $C_2H_5$ | $CH_3$ | $C_2H_5$ | S | 71 | $n_D^{23}$:1.5048 |
| 16 | H | $C_2H_5$ | $C_2H_5$ | $OC_2H_5$ | O | 72 | $n_D^{23}$:1.4538 |
| 17 | H | H | $C_2H_5$ | $OC_2H_5$ | O | 78 | $n_D^{23}$:1.4709 |
| 18 | H | H | $C_2H_5$ | $OC_2H_5$ | S | 74 | $n_D^{23}$:1.4950 |
| 19 | H | H | $CH_3$ | $OCH_3$ | S | 54 | $n_D^{23}$:1.5072 |
| 20 | H | H | $C_2H_5$ | $C_2H_5$ | S | 87 | $n_D^{23}$:1.5123 |
| 21 | H | H | $C_2H_5$ | $SC_3H_7$-n | S | 71 | $n_D^{23}$:1.5268 |
| 22 | H | H | $C_3H_7$-iso | $CH_3$ | S | 78 | $n_D^{23}$:1.5110 |
| 23 | H | H | $C_2H_5$ | $CH_3$ | S | 73 | $n_D^{23}$:1.5150 |
| 24 | H | H | $C_2H_5$ | phenyl | S | 70 | $n_D^{23}$:1.5581 |
| 25 | H | H | $CH_3$ | $C_2H_5$ | S | 82 | $n_A^{23}$:1.5199 |
| 26 | H | H | $C_2H_5$ | $C_4H_9$-sec. | S | 90 | $n_D^{23}$:1.5102 |
| 27 | H | H | $CH_3$ | $OC_3H_7$-n | S | 59 | $n_D^{23}$:1.5321 |
| 28 | Cl | H | $C_2H_5$ | $OC_2H_5$ | S | 89 | $n_D^{23}$:1.5061 |
| 29 | Cl | H | $C_2H_5$ | $C_2H_5$ | S | 84 | $n_D^{23}$:1.5169 |
| 30 | Cl | H | $C_2H_5$ | phenyl | S | 76 | $n_D^{23}$:1.5611 |
| 31 | Cl | H | $CH_3$ | $OC_3H_7$-n | S | 80 | $n_D^{23}$:1.5080 |
| 32 | Cl | H | $C_2H_5$ | $OC_3H_7$-n | S | 81 | 103° C. (m.pt) |
| 33 | H | $C_3H_7$-iso | $C_2H_5$ | $OC_2H_5$ | S | 95 | $n_D^{23}$:1.4880 |
| 34 | H | $C_3H_7$-iso | $C_2H_5$ | $C_2H_5$ | S | 85 | $n_D^{23}$:1.4967 |
| 35 | H | $C_3H_7$-iso | $C_2H_5$ | $SC_3H_7$-n | S | 90 | $n_D^{23}$:1.5130 |
| 36 | H | $C_3H_7$-iso | $CH_3$ | $OCH_3$ | S | 78 | $n_D^{23}$:1.4960 |
| 37 | H | $C_3H_7$-iso | $C_3H_7$-iso | $CH_3$ | S | 82 | $n_D^{23}$:1.4940 |
| 38 | H | $C_3H_7$-iso | $C_2H_5$ | phenyl | S | 74 | $n_D^{23}$:1.5380 |
| 39 | H | $C_3H_7$-iso | $C_2H_5$ | $OC_2H_5$ | O | 76 | $n_D^{23}$:1.4660 |
| 40 | H | $C_3H_7$-iso | $C_2H_5$ | $CH_3$ | S | 79 | $n_D^{23}$:1.4983 |
| 41 | H | $C_3H_7$-iso | $CH_3$ | $C_2H_5$ | S | 88 | $n_D^{23}$:1.5024 |
| 42 | H | $C_3H_7$-iso | $C_2H_5$ | $C_4H_9$-sec. | S | 89 | $n_D^{23}$:1.4984 |
| 43 | H | $C_3H_7$-iso | $C_2H_5$ | $OC_3H_7$-n | S | 95 | $n_D^{23}$:1.4865 |
| 44 | H | $C_5H_{11}$-n | $CH_3$ | $OC_2H_5$ | S | | |
| 45 | H | H | $C_5H_{11}$-sec. | $OC_2H_5$ | S | | |
| 46 | H | H | $CH_3$ | $OC_5H_{11}$-n | S | | |
| 47 | H | H | $CH_3$ | $SC_4H_9$-n | S | | |

The activity of the compounds of this invention is illustrated by the following biotest examples in which the compounds according to the present invention are each identified by the number (given in brackets) from the preparative examples hereinabove.

The known comparison compounds are identified as follows:

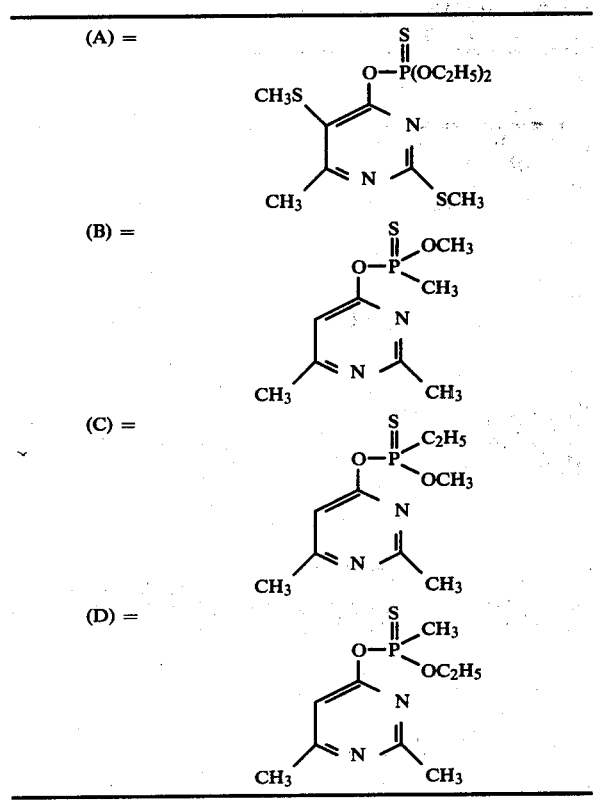

EXAMPLE 3

$LT_{100}$ test for Diptera

Test insects: *Aedes aegypti*

Solvent: Acetone

The active compound was dissolved in the solvent at a rate of 2 g per liter. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. About 25 test insects were then placed in the Petri dish and it was covered with a glass lid.

The condition of the test insects was continuously observed. The time which was necessary for 100% destruction was determined.

The active compounds, the concentrations of the active compounds and the times at which there was 100% destruction can be seen from the following table:

Table 3

($LT_{100}$ test for *Diptera/Aëdes aegypti*)

| Active compound | Active compound concentration of the solution, in % | $LT_{100}$ in minutes (') or hours (h) |
|---|---|---|
| (A) | 0.02 | $3^h = 0$ |
| (11) | 0.02 | 180' |
| (16) | 0.02 | 120' |
| (4) | 0.02 | 120' |
| (17) | 0.02 | 120' |
| (22) | 0.02 | 60' |
| (23) | 0.02 | 60' |
| (25) | 0.02 | 120' |
| (1) | 0.02 | 60' |

EXAMPLE 4

Mosquito larvae test

Test insects: *Aedes aegypti* larvae

Solvent: 99 parts by weight of acetone

Emulsifier: 1 part by weight of benzylhydroxydiphenyl polyglycol ether

To produce a suitable preparation, the active compound was dissolved, at a rate of 2 g per liter, in the solvent containing the amount of emulsifier stated above. The solution thus obtained was diluted with water to the desired lower concentrations.

The aqueous preparations of the active compounds were placed in glass vessels and about 25 mosquito larvae were then placed in each glass vessel.

After 24 hours, the degree of destruction was determined as a percentage. 100% meant that all of the larvae were killed. 0% meant that none of the larvae were killed.

The active compounds, the concentrations of the active compounds and the results can be seen from the following table:

Table 4

(Mosquito larvae test/*Aëdes aegypti*)

| Active compound | Active compound concentration of the solution, in ppm | Degree of destruction in % |
|---|---|---|
| (B) | 1 | 0 |
| (C) | 1 | 0 |
| (D) | 1 | 0 |
| (9) | 1 | 95 |
| (10) | 1 | 100 |
| (13) | 1 | 100 |
| (14) | 1 | 90 |
| (2) | 1 | 100 |
| (3) | 1 | 100 |
| (5) | 1 | 100 |
| (6) | 1 | 90 |
| (18) | 1 | 100 |
| (19) | 1 | 100 |
| (20) | 1 | 100 |
| (21) | 1 | 100 |
| (24) | 1 | 100 |
| (27) | 1 | 100 |

EXAMPLE 5

Plutella test

Solvent: 3 parts by weight of dimethylformamide

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% meant that all of the caterpillars were killed whereas 0% meant that none of the caterpillars were killed.

The active compounds, the concentrations of the active compounds, the evaluation times and the results can be seen from the following table:

Table 5

| (Plutella test) | | |
|---|---|---|
| Active compound | Active compound concentration in % | Degree of destruction in % after 3 days |
| (A) | 0.1 | 80 |
|  | 0.01 | 0 |
| (19) | 0.1 | 100 |
|  | 0.01 | 100 |
| (6) | 0.1 | 100 |
|  | 0.01 | 100 |
| (18) | 0.1 | 100 |
|  | 0.01 | 100 |
| (17) | 0.1 | 100 |
|  | 0.01 | 100 |
| (1) | 0.1 | 100 |
|  | 0.01 | 100 |
| (7) | 0.1 | 100 |
|  | 0.01 | 100 |
| (9) | 0.1 | 100 |
|  | 0.01 | 100 |
| (3) | 0.1 | 100 |
|  | 0.01 | 100 |
| (25) | 0.1 | 100 |
|  | 0.01 | 100 |
| (15) | 0.1 | 100 |
|  | 0.01 | 100 |
| (20) | 0.1 | 100 |
|  | 0.01 | 100 |
| (2) | 0.1 | 100 |
|  | 0.01 | 100 |
| (10) | 0.1 | 100 |
|  | 0.01 | 100 |
| (34) | 0.1 | 100 |
|  | 0.01 | 100 |
| (27) | 0.1 | 100 |
|  | 0.01 | 100 |
| (5) | 0.1 | 100 |
|  | 0.01 | 100 |
| (22) | 0.1 | 100 |
|  | 0.01 | 100 |
| (4) | 0.1 | 100 |
|  | 0.01 | 100 |
| (12) | 0.1 | 100 |
|  | 0.01 | 100 |
| (37) | 0.1 | 100 |
|  | 0.01 | 100 |
| (21) | 0.1 | 100 |
|  | 0.01 | 100 |
| (13) | 0.1 | 100 |
|  | 0.01 | 100 |
| (35) | 0.1 | 100 |
|  | 0.01 | 100 |
| (24) | 0.1 | 100 |
|  | 0.01 | 100 |
| (8) | 0.1 | 100 |
|  | 0.01 | 100 |
| (14) | 0.1 | 100 |
|  | 0.01 | 100 |

EXAMPLE 6

Tetranychus test (resistant)
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all of the spider mites were killed whereas 0% meant that none of the spider mites were killed.

The active compounds, the concentrations of the active compounds, the evaluation times and the results can be seen from the following table:

| (Tetranychus test/resistant) | | |
|---|---|---|
| Active compound | Active compound concentration in % | Degree of destruction in % after 2 days |
| (A) | 0.1 | 100 |
| (39) | 0.1 | 99 |
| (23) | 0.1 | 100 |
| (3) | 0.1 | 100 |
| (22) | 0.1 | 100 |
| (35) | 0.1 | 100 |

EXAMPLE 7

Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The amount of active compound was intimately mixed with the soil. The concentration of the active compound in the preparation was practically immaterial, the only decisive factor being the amount by weight of active compound per unit volume of soil, which is quoted hereinafter in ppm (=mg/l). The treated soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all of the test insects had been killed and was 0% if exactly as many test insects were still alive as in the case of the untreated control.

The active compounds, the amounts used and the results can be seen from the table which follows:

Table 7

| (*Phorbia antiqua* grubs in the soil) | |
|---|---|
| Active compound | Degree of destruction in % at an active compound concentration of 10 ppm |
| (A) | 0 |
| (B) | 0 |

Table 7-continued
(Phorbia antiqua grubs in the soil)

| Active compound | Degree of destruction in % at an active compound concentration of 10 ppm |
| --- | --- |
| (9) | 100 |
| (11) | 100 |
| (12) | 100 |
| (15) | 100 |
| (1) | 100 |
| (33) | 100 |
| (34) | 100 |
| (35) | 100 |
| (36) | 100 |
| (37) | 100 |
| (38) | 100 |
| (40) | 100 |
| (41) | 100 |
| (43) | 100 |

EXAMPLE 8

Test insect: Tenebrio molitor larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The amount of active compound was intimately mixed with the soil. The concentration of the active compound in the preparation was practically immaterial, the only decisive factor being the amount by weight of active compound per unit volume of soil, which is quoted hereinafter in ppm (=mg/l). The treated soil was filled into pots and the pots were left to stand at room temperature.

After 24 hours the test insects were introduced in to the treated soil and after a further 2 to 7 days the degree of effectiveness of the active compound was determined in % by counting the dead and the live test insects. The degree of effectiveness was 100% if all of the test insects had been killed and was 0% if exactly as many test insects were still alive as in the case of the untreated control.

The active compounds, the amounts used and the results can be seen from the table which follows:

Table 8
(Tenebrio molitor larvae in the soil)

| Active compound | Degree of destruction in % at an active compound concentration of 5 ppm |
| --- | --- |
| (A) | 0 |
| (B) | 0 |
| (20) | 100 |
| (18) | 100 |
| (25) | 100 |
| (26) | 100 |
| (27) | 100 |

EXAMPLE 9

Test on blowfly larvae
Screening test on Lucilia cuprina/tube in vitro
Test animal: Freshly hatched, about 12–24 hours old, sensitive blowfly larvae (Lucilia cuprina).

Test method: About 20–30 larvae per concentration were introduced into a series of preparations (100, 10 and 1 ppm). For this purpose, larvae were placed on cottonwool plugs (diameter 1.7 cm, height 1 cm, Messrs Rescheisen u. Co., Ulm) contained in glass tubes (white diffusing tubes, 43/44×23/24 mm, made from Bunder glass, Article No. 7,301,009), the plugs having beforehand been moistened with 2.5 ml of a 25% strength suspension of bonemeal in water.

0.5 ml of the preparation to be tested was then pipetted onto these moistened cottonwool plugs. The tubes were then transferred to, and kept in, a climatically controlled room (27°±1° C., humidity±5%). The action was examined after 24 hours.

Test criteria: The criterion of the action was the occurrence of death of the treated larvae.

The active compounds, active compound concentrations and results can be seen from the table which follows:

Table 9
(Test on blowfly larvae (Lucilia cuprina))

| Active compound | Active compound concentration in ppm | Degree of destruction in % |
| --- | --- | --- |
| (34) | 100 | 100 |
|  | 30 | 100 |
|  | 10 | 100 |
| (36) | 100 | 100 |
|  | 30 | 100 |
|  | 10 | 100 |
|  | 3 | 100 |
| (40) | 100 | 100 |
|  | 10 | 100 |
| (41) | 100 | 100 |
|  | 30 | 100 |
|  | 10 | 100 |
|  | 3 | >50 |
|  | 1 | >50 |

It will be appreciated that the instant specification and claims are set forth by way of illustration and not limitation, and that various modifications and changes may be made without departing from the spirit and scope of the present invention.

What is claimed is:

1. An O-alkyl-O-[6-tert.-butylpyrimidin(4)yl](thiono)(thiol)-phosphoric(phosphonic) acid ester of the formula $$\begin{array}{c} X \\ \parallel \\ O-P-OR^2 \\ | \\ R^3 \end{array}$$

(with R on the ring, tert.-C$_4$H$_9$ on the ring, and N—R$^1$ position)

in which
R is hydrogen, halogen or alkyl,
R$^1$ is hydrogen or alkyl,
R$^2$ is alkyl,
R$^3$ is alkyl, alkoxy, alkylthio or phenyl, and
X is oxygen or sulphur, the various alkyl moieties having 1 to 6 carbon atoms.

2. A compound according to claim 1, in which
R is hydrogen or chlorine,
R$^3$ is alkoxy or alkylthio each with 1 to 6 carbon atoms, or phenyl, and
X is sulphur.

3. A compound according to claim 1, wherein the compound is O,O-diethyl-O-[2-methyl-6-tert.-butylpyrimidin(4)yl]-thionophosphoric acid ester of the formula

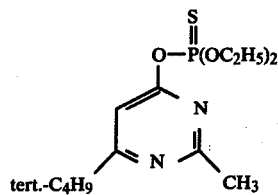

4. A compound according to claim 1, wherein the compound is O,O-dimethyl-O-[2-methyl-6-tert.-butyl-pyrimidin(4)yl]-thionophosphoric acid ester of the formula

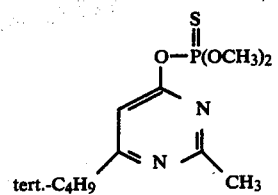

5. A compound according to claim 1, wherein the compound is O-methyl-O-[6-tert.-butyl-pyrimidin(4)yl]-ethanethionophosphonic acid ester of the formula

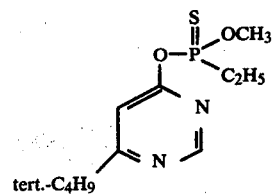

6. A compound according to claim 1, wherein the compound is O-ethyl-O-[2-isopropyl-6-tert.-butyl-pyrimidin(4)yl]-methanethio-nophosphonic acid ester of the formula

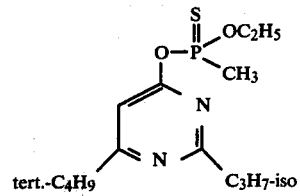

7. A compound according to claim 1, wherein the compound is O-methyl-O-[2-isopropyl-6-tert.-butyl-pyrimidin(4)yl]-ethanethionophosphonic acid ester of the formula

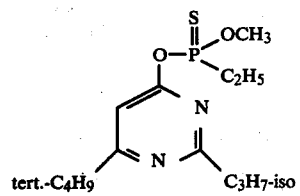

8. An arthropodicidal composition containing as active ingredient an arthropodicidally effective amount of a compound according to claim 1 in admixture with a diluent.

9. A method of combating arthropods which comprises applying to the arthropods, or to a habitat thereof, an arthropodicidally effective amount of a compound according to claim 1.

10. The method according to claim 9 in which said compound is
O,O-diethyl-O-[2-methyl-6-tert.-butyl-pyrimidin(-4)yl]-thionophosphoric acid ester,
O,O-dimethyl-O-[2-methyl-6-tert.-butyl-pyrimidin(-4)yl]-thionophosphoric acid ester,
O-methyl-O-[6-tert.-butyl-pyrimidin(4)yl]-ethanethionophosphonic acid ester,
O-ethyl-O-[2-isopropyl-6-tert.-butyl-pyrimidin(4)yl]-methanethionophosphonic acid ester, or
O-methyl-O-[2-isopropyl-6-tert.-butyl-pyrimidin(-4)yl]-ethanethionophosphonic acid ester.